United States Patent [19]

Adell

[11] Patent Number: 4,983,334
[45] Date of Patent: Jan. 8, 1991

[54] METHOD OF MAKING AN ORTHODONTIC APPLIANCE

[75] Inventor: Loren S. Adell, 6207 Telluride La., Dallas, Tex. 75252

[73] Assignees: Loren S. Adell; Michael Adell, both of Sunnyvale, Tex.

[21] Appl. No.: 274,012

[22] Filed: Nov. 21, 1988

Related U.S. Application Data

[62] Division of Ser. No. 901,729, Aug. 28, 1986, abandoned.

[51] Int. Cl.$^5$ ............................................. A61C 13/00
[52] U.S. Cl. ....................................... 264/16; 264/138; 264/322; 433/6
[58] Field of Search .................. 264/16, 322, 138, 161, 264/162; 433/18, 24, 196, 6

[56] References Cited

U.S. PATENT DOCUMENTS

| | | | |
|---|---|---|---|
| 4,055,895 | 11/1977 | Huge | 32/14 B |
| 4,401,616 | 8/1983 | Wagner | 264/138 |
| 4,690,787 | 9/1987 | Fasnacht | 264/16 |

Primary Examiner—James Lowe
Assistant Examiner—Christopher A. Fiorilla
Attorney, Agent, or Firm—George L. Boller

[57] ABSTRACT

A method of making a dental appliance made of an elasticized acrylic containing embedded nylon fibers including the steps of heating the thermoplastic material, forming it onto a dental cast, and cooling it to a rigid state. The fibers may be arranged in various patterns within the elasticized acrylic and it is the fibers which act on the arch through the elasticized acrylic. The appliance may be used as a tooth positioner, a retainer, a splint, or a base plate.

4 Claims, 5 Drawing Sheets

METHOD OF MAKING AN ORTHODONTIC APPLIANCE

This is a divisional of co-pending application Ser. No. 06/901,729 filed on Aug. 28, 1986, now abandoned.

BACKGROUND AND SUMMARY OF THE INVENTION

This invention relates to dental appliances. More specifically, it relates to a new and improved appliance comprising a unique organization and arrangement of synthetic materials. Various embodiments of the appliance are disclosed, including a tooth positioner, a retainer, a splint and a base plate.

Historically, orthodontic appliances for performing tooth movement have involved the use of metal parts such as metal bands, metal brackets and metal arch wires. Because of the inherent nature of these components, the presence of such appliances in the mouth of an individual is readily apparent in the individual's everyday activities.

In one respect the present invention is an improvement over these appliances because it avoids the prominent use of metal parts. Hence it presents a less noticeable appearance, but is nonetheless fully capable of performing tooth movement in order to achieve desired orthodontic corrections.

Further aspects of the invention are that it can be embodied in a number of ways depending upon the needs of the particular type of correction to be performed, it can be fabricated in a more efficient manner than prior appliances, and when worn by an individual, it can provide improved comfort and a better fit.

While the principal objective relates to the applicances per se, related aspects of the invention include apparatus and methods for fabricating the appliances, and to the materials used in fabricating the appliances.

A preliminary novelty search in connection with the present invention has not revealed any pertinent prior art. The only reference of any interest is U.S. Pat. No. 4,055,895. That patent discloses an appliance in which a mouthpiece is molded around tensioned bands. In practice it is believed that such an appliance is discomforting to wear because it is in the form of a mouthpiece. Likewise it has a limited degree of effectiveness because it is adapted specifically to treatment of one particular condition, and at that it is unclear how well that treatment can be performed by the appliance in practice. Such an appliance would occupy the whole mouth and therefore it is unlikely to be worn for extended periods during everyday use. It is obviously very noticeable.

U.S. Pat. No. 4,224,021 shows a rigid, transparent, plastic band which is anchored by C-clasps and special fasteners to the molars.

Thus the present invention, as will be hereinafter seen, possesses most significant advantages over the existing state-of-the-art. A presently preferred embodiment of the invention will be hereinafter prescribed with reference to the accompanying drawings which portray the best means contemplated at the present time in carrying out the invention.

DESCRIPTION OF PREFERRED EMBODIMENT

Figure 1:
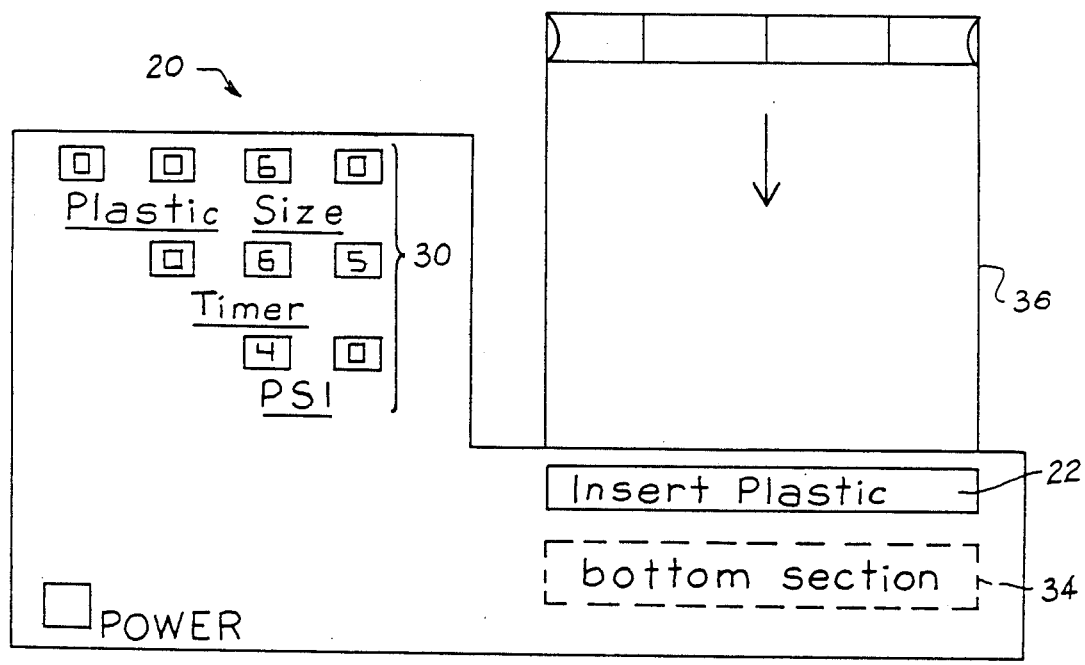
FIGS. 1 and 2 are front and top views respectively, somewhat diagrammatic, of apparatus for fabricating an appliance embodying principles of the invention.
Figure 2:
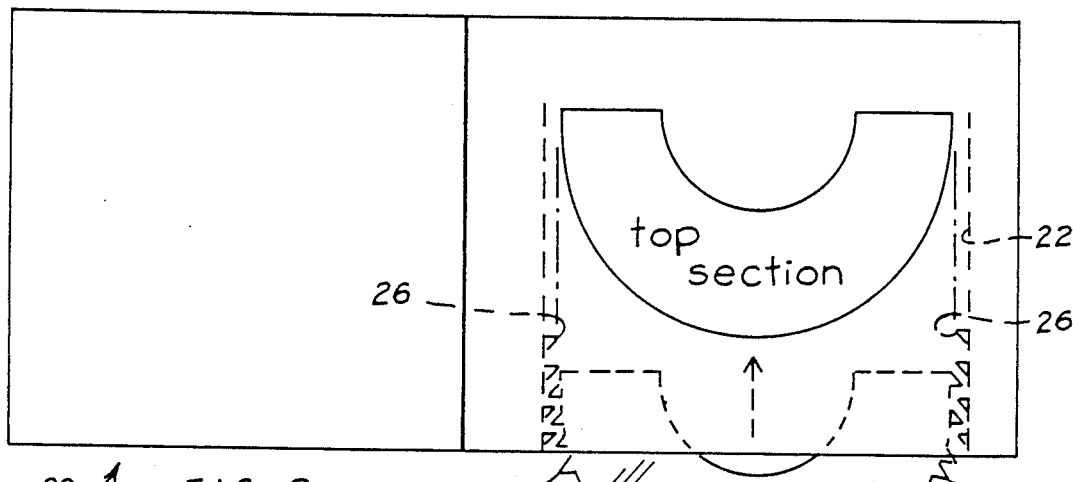

FIGS. 1 and 2 illustrate apparatus 20 which is useful in making appliances according to principles of the invention. Apparatus 20 is illustrated in somewhat diagrammatic fashion since in certain respects it is conventional. The apparatus 20 comprises a receptacle 22 into which a piece of material 24 is inserted for processing.

The piece of material 24 constitutes a blank, or preform, for the orthodontic appliance which is to be fabricated. The details of this piece will be subsequently described.

Piece 24 is illustrated in a flat generally U-shaped form which fits into receptacle 22. The receptacle 22 may be considered to be in the form of a slot which receives the piece 24. There are a series of serrations 26 in the sides of the receptacle and these serrations 26 cooperate with corresponding serrations 28 which are incorporated into the edges of the piece 24. The serrations serve to provide an interlocking feature which is useful in the fitting of the piece into the receptacle.

Apparatus 20 further comprises a series of controls, 30 generally, which are used to control the operation of the apparatus in acting upon the piece 24. These controls include adjustments for the particular thickness of the piece, a timer and a pressure control. The apparatus 20 further comprises a bottom section 34 which contains a cast (not shown) of a dental arch which has been derived from the patient for whom the appliance is to be created. The arch is supported within the bottom section directly below the receptacle 22 so as to be directly below the U-shaped piece 24.

The operation of apparatus 20 initially includes heating of the piece 24 to bring it to a semi-plastic or plastic condition. During this time, the side margins of the sheet are held via the serrations. Upon the attainment of a semi-plastic or plastic condition after an appropriate amount of time based upon the thickness and particular composition of the material, a pressure applying means 36 is operated causing the material 24 to be formed onto the cast. Hence the material 24 will now assume a shape complementary to that of the cast. The material is then allowed to cool so that it returns to its original more rigid condition. As such it will have a form which exactly corresponds to the position of teeth in the cast. The part may then be trimmed as desired around the edges so that the finished appliance will fit the patient.

The cast represents typically a final tooth position which is to be achieved after completion of use of the appliance in the patient. One way the cast can be formed is by taking an impression of the existing arch of the patient and then resetting those teeth in the arch which are to be moved. In this way the finished appliance will not have an exact fit because of the difference between the existing position of the teeth to be moved and their future position as defined by the appliance after it has been made on the cast containing the reset teeth. When the appliance is applied to the arch, it will resiliently deform due to the non-exact fit, and therefore act to exert corrective forces on the teeth to be moved.

Figure 4:
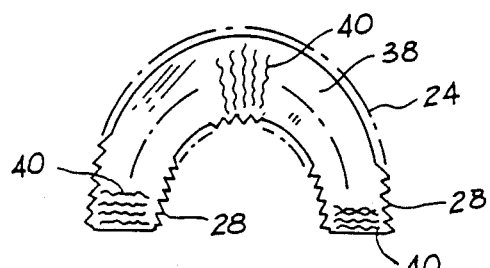
FIGS. 3 and 4 are plan views of two different embodiments of parts before processing by the apparatus of FIGS. 1 and 2.
Figure 3:
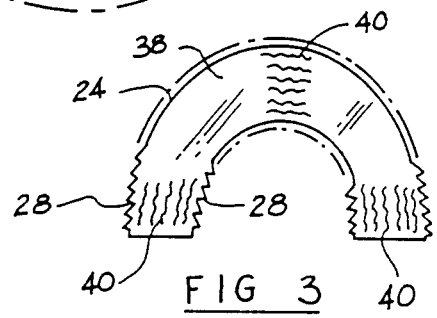

One of the features of the invention is that the piece of material 24 contains a particular composition which enables the desired corrective forces to be exerted in the finished appliance. FIGS. 3 and 4 portray representative forms. The composition comprises a main body 38 of a suitable synthetic material, for example, clear elasticized acrylic. Internally of this body of material are individual fibers 40 which are arranged in patterns. FIG. 3 illustrates an example with the fibers 40 having circumferential orientation. FIG. 4 illustrates a pattern of fibers having a radial orientation extending around the U-shaped piece. While the base material for the piece 24 will have a certain amount of resiliency, it alone does not develop the tooth movement forces. It is the individual fibers 40 which are within the base material which exert primary tooth movement forces when the appliance is in use on a patient; the resilient character of the material of main body 38 serves to locate the fibers and to accommodate their tooth movement actions.

Figure 5:
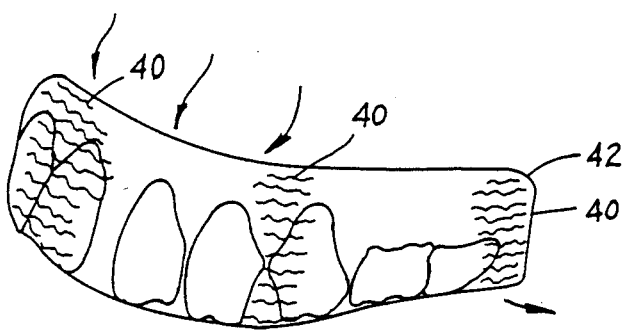
FIGS. 5 and 6 are views of appliances formed from the parts of FIGS. 3 and 4 respectively, and shown in orthodontic use.
Figure 6:
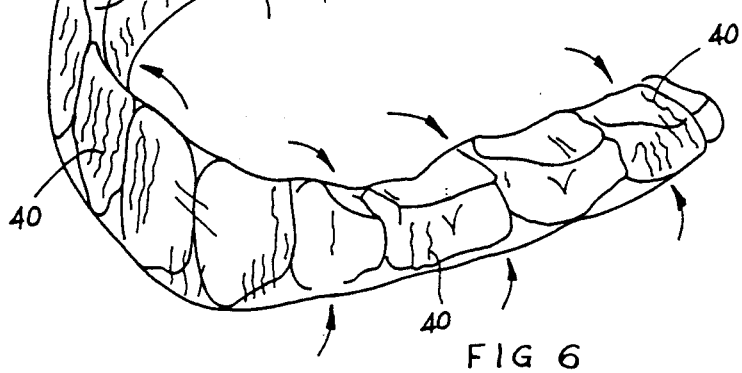

FIGS. 5 and 6 portray representative appliances 42, 44 fabricated from the pre-forms of FIGS. 3 and 4 on an upper and lower arch respectively. In FIG. 6 the individual fibers 40 extend vertically on the sides and horizontally across the crowns of the teeth. In FIG. 5 the fibers 40 extend mesial-distally in the buccal-labial and lingual sides of the appliances and similarly along the crowns of the teeth.

Figure 7:
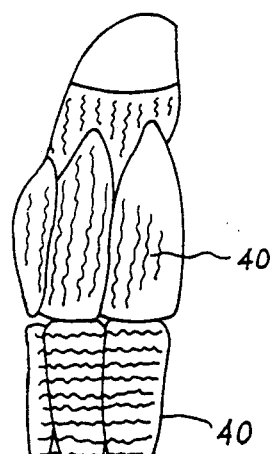
FIG. 7 is a fragmentary frontal view illustrating further orthodontic use.

FIG. 7 illustrates an opposite configuration where the FIG. 4 orientation of fibers 40 is used in an appliance applied to the upper arch while the bottom arch contains an appliance in which the fibers run in the manner of FIGS. 3 and 5.

Formation of an appliance in apparatus 20 will be effective to cause the individual fibers 40 to be activated to force-applying conditions when the appliance is in use in a patient. This can be accomplished by various means, either singly, or in combination. For example a simple mechanical tensioning due to material deformation is one way. This was described above.

It is also possible to utilize heat applied to the part in conjunction with inherent characteristics of the material of the fibers. For example, when certain materials in fiber form are heated and then cooled, they will experience a contraction from their original state. Hence, appropriately designed fibers embedded in the base material can exert tension by contraction. Such fibers acting through the acrylic material within which they are embedded, will exert corrective forces in the appliance. Consequently, this type of corrective action can be developed in the appliance to be effective to move teeth when the appliance is in use on a patient. When this type of action is developed, the cast will typically not represent final tooth position because the appliance, as formed and cooled onto the cast will have fibers in tension, and when it is removed from the cast, it may slightly relax the tension and therefore possibly assume just a slightly different shape from the cast.

Figure 8:
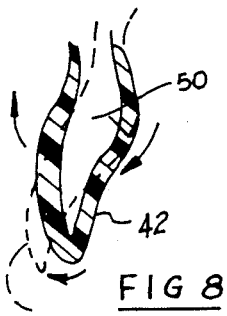

FIG. 8 illustrates a form of action which is utilized to torque an individual tooth 50 outwardly. The solid line position represents the conditioning of the appliance fitting on the arch. The broken line represents the ideal set-up toward which the appliance is effective to move the tooth.

Figure 9:
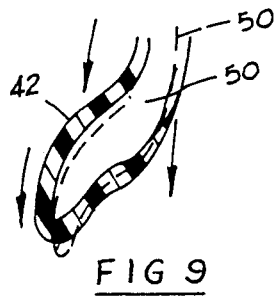

FIG. 9 portrays another form of action with the broken line representing the ideal set-up toward which the appliance is moving the tooth.

Figure 11:
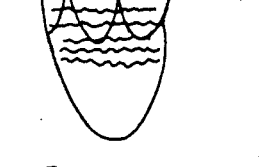
FIGS. 8, 9, 10 and 11 are transverse cross sectional views illustrating various types of tooth movement which is performed by the appliance.
Figure 10:
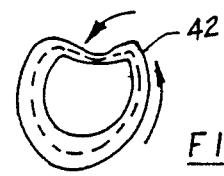

FIG. 10 portrays action on a molar tooth and shows that torquing is possible on posterior teeth. In these embodiments it is to be observed that the appliance will exert an action on each individual tooth through the portion of the appliance which is engaged with the tooth. This independence is illustrated in FIG. 11 which shows each tooth is acted upon independently by the fibers acting on it.

Figure 12:
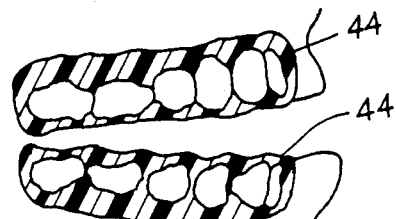
FIG. 12 is a side view illustrating appliances in orthodontic use.

FIG. 12 shows that the appliance can also serve to maintain an existing tooth position, i.e. retention. For example, after a treatment procedure which has positioned teeth to an ideal set-up, an appliance can be fabricated corresponding exactly to the ideal set-up. Neither the fibers nor the acrylic base material will be significantly tensioned, but any attempted tooth movement will be resisted by the appliance. Hence while the appliance is principally useful for tooth movement, it also has the ability to maintain tooth position. Even if the appliance is not worn for awhile and there is some tooth movement, the appliance can still flex slightly to fit and serve to exert forces to bring the teeth back to the desired position.

In general, one appliance will serve to perform limited tooth movement, as distinguished from large amounts of tooth movement. Therefore, in any given person, one or more appliances may have to be fabricated during the course of treatment. This will depend upon how much correction is needed. By using thermoplastic materials it is possible to "re-cycle" an existing appliance for an individual rather than making a brand new one. In other words, for example, after an appliance has performed a certain amount of tooth movement, it can be re-heated and formed into a new cast, and then cooled for continued use.

Figure 13:
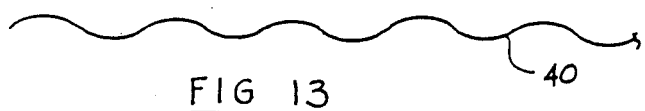
FIGS. 13, 14 and 15 are enlarged views illustrating much greater detail of various forms of certain elements in the parts of FIGS. 3 and 4.
Figure 14:
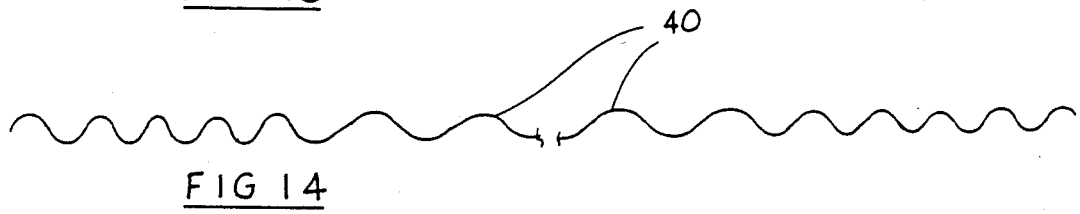
Figure 15:
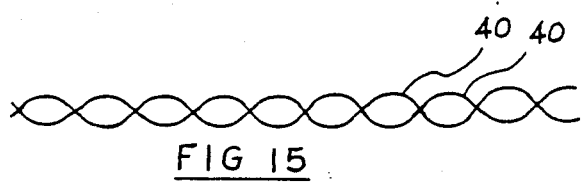

FIGS. 13, 14, and 15 illustrate representative forms of individual fibers 40. FIG. 13 shows the fiber which possesses a series of S-shaped formations. By making the formations identical, an equal force distribution is applied by the fiber in the appliance.

While it is contemplated that various materials may be used for the fibers, a presently preferred material is nylon. It is known that when heated in certain ways, nylon will tend to develop contraction forces. Therefore, the heating and forming of the material to a dental arch, followed by cooling, can result in the development of forces for imparting tooth movement when the appliance is in place.

FIG. 14 illustrates a similar configuration but in which different spacing distances are provided between certain of the formations. For example, in the middle segment the curves are further apart than along the end segments. This will result in a different amount of force in different regions of the fiber when it is active in the appliance.

FIG. 15 illustrates a double stranded fiber also of curved formation which may be twisted together. An advantage of this configuration will allow more movement of the teeth and may afford a greater force action.

Figure 16:
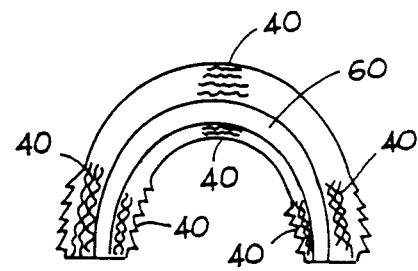
FIGS. 16 and 17 are views of another embodiment of appliance containing additional constructional features.
Figure 17:
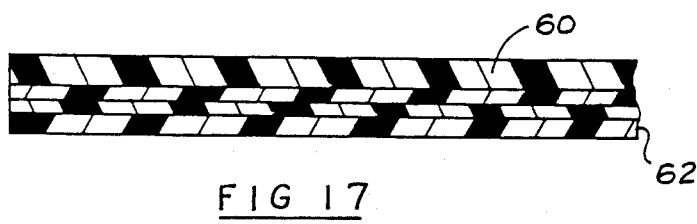

FIGS. 16 and 17 illustrate another form of the appliance which is constructed of several different layers. The occlusal surface of the appliance is constructed by a semi-hard plastic 60 so that the appliance can act as a splint which precludes contact with the occlusal surface of the opposing arch. Fibers are arranged on the buccal-labial and lingual sides of the appliance.

Figure 18:
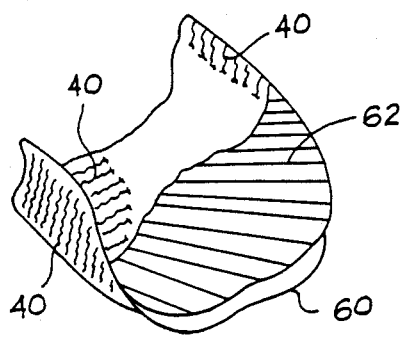
FIGS. 18 and 19 are views of additional constructional features.
Figure 19:
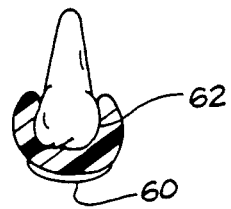

The bottom layer 62 is a gummy grade of plastic which is to allow a tighter, more intricate seal with the tooth structure on the arch to which the appliance is fitted. This would allow more pressure to be applied when needed for relaxing muscle tension. The embodiment of FIGS. 18 and 19 is somewhat similar to that of FIGS. 16 and 17 but rather than the gummy surface on the interior, the embodiment of FIGS. 18 and 19 has an inner clear insulated material. This would allow the teeth to have more cushioning as well as more retention for the process of moving tooth structure. The outer layer forms the splint and the middle layer is the material which contains the fibers.

Figure 20:
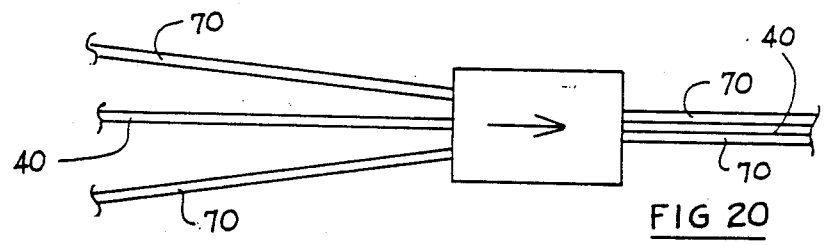
FIGS. 20 and 21 are views illustrating one possible way of fabricating the material of the appliance.
Figure 21:
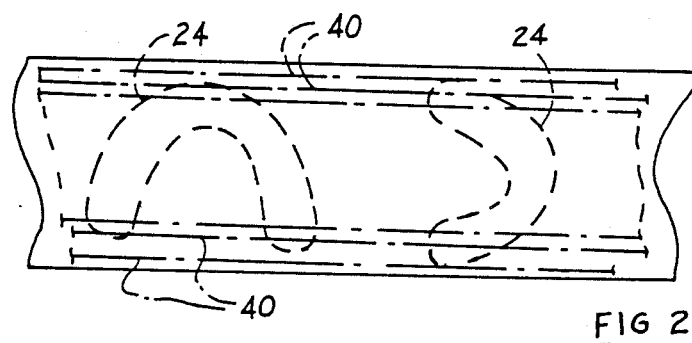

FIGS. 20 and 21 depict one way of fabricating the material from which the appliance is constructed. According to this particular way of making the material, the individual fibers 40 are extruded between extruded layers of base material 70 such that the resultant construction is bonded together in an integral form. The length of the fibers will be parallel to the direction of extrusion. The dimensions of the fibers in relation to the thicknesses of the sandwiching layers 70 will be such that appropriate forces are developed in the appliance, when in use, in accordance with the tooth positioning or tooth maintenance procedures described above.

The resultant product is shown in FIG. 21 in what may be considered as a sheet form. The orientation of the individual fibers 40 in a particular piece 24 cut from the sheet will depend upon the relative orientation of the sheet when cut. FIG. 21 illustrates two possible ways to cut the pieces 24 each at 90 degrees to the other. It is to be understood that these are merely representative illustrations.

Figure 22:
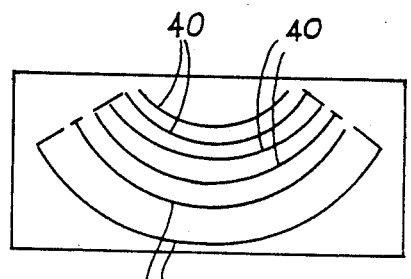
FIG. 22 is a view of another possible way of fabricating the material.
Figure 23:
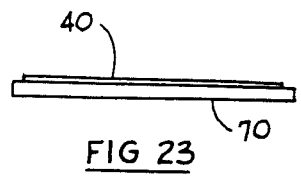
FIGS. 23 and 24 are views of two types of materials resulting from the procedure of FIG. 22.
Figure 24:
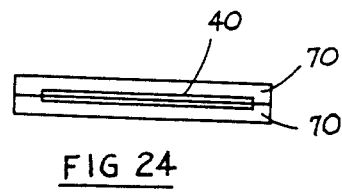

FIGS. 22, 23, and 24 illustrate another way for fabricating the material of the appliance. Here the individual fibers 40 are deposited on a substrate or base in a desired pattern. The fibers may be deposited by any conventional procedure, such as by extrusion. Since this substrate is not being continuously extruded along a line, as was the case for FIGS. 20 and 21, there is a greater versatility in orienting the individual fibers on the substrate. The illustration of FIG. 22 portrays a construction in which the individual fibers follow the general form of the arch. In the finished appliance the fibers would all be essentially horizontal. Once again it is to be appreciated that this is merely representative and that other layouts for individual fibers are contemplated within the scope of the invention.

The fabrication procedure involves a suitable interaction between the substrate and the individual fibers such that the fibers become encapsulated in the base material, or otherwise essentially integral with the base material. This may involve the use of adhesives in some instances.

In FIG. 23 the fibers are not fully embedded in the manner of FIGS. 20 and 21.

If it is desired to fully encapsulate the fibers, then an overlying layer of suitable material (see FIG. 24) may be applied so that the resultant material has the fibers encapsulated in a sandwiched manner like that in FIGS. 20 and 21.

Figure 25:
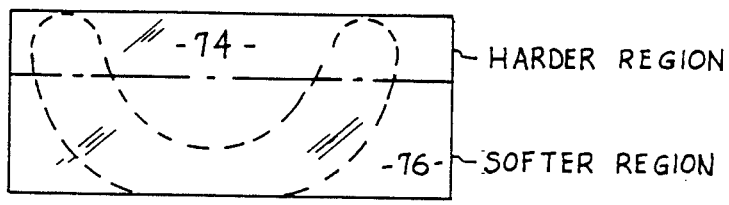
FIG. 25 is a view of still another way of fabricating material.
Figure 26:
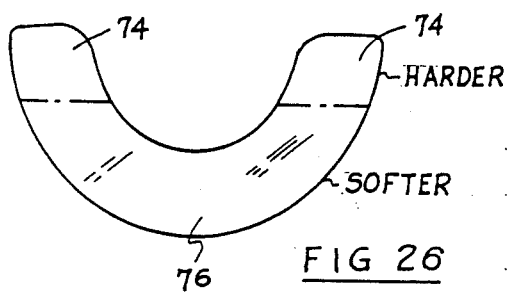
FIG. 26 is a view of a piece cut from the material of FIG. 25.
Figure 27:
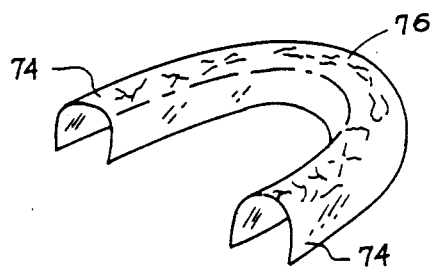
FIG. 27 is a view of a formed appliance.

The base material characteristics may also be employed in particular ways. FIG. 25 illustrates a construction in which the base material is less resilient, or harder, along the regions 74 of the appliance which fit onto the molar regions of the arch. The mesial region 76 of the appliance is of a softer, somewhat more resilient base material. Hence when this appliance is cut from the material of FIG. 25 and formed to the final shape (see FIGS. 26 and 27), the harder, less resilient regions serve to anchor the appliance on the molars so that the mesial region is effective in moving the incisors and/or cuspids. The characteristics can be achieved in different ways such as by varying the thickness, density, or durometer of the base material, and/or the size, thickness, shape, or durometer of the fibers.

Figure 28:
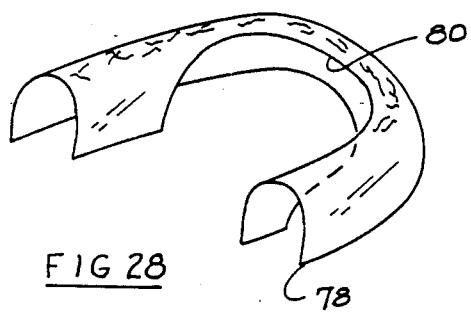
FIG. 28 is a view of a modified form of FIG. 27.

The appliances which have been illustrated have so far been shown in substantially full covering relationship to lingual and labial sides of the arch, and to the crowns of the teeth. Other forms of appliances embodying principles of the invention are contemplated which do not have such full covering. One of these 78 is shown in FIG. 28 where a notch 80 has been cut in the lingual region mesially of the molars. The notch does not extend over the crowns of the teeth, therefore this modified, notched-out, form of appliance, like the forms previously described, still has an occlusal surface, but other forms of the appliance can omit such an occlusal surface, if desired. The appliance can be formed with holes for the crowns of the teeth and yet can still have substantial effect for at least certain types of tooth movement. By closely forming the appliance to the individual teeth, horizontal fibers may be considered to have a certain anchoring at the inter-proximal areas.

Figure 29:
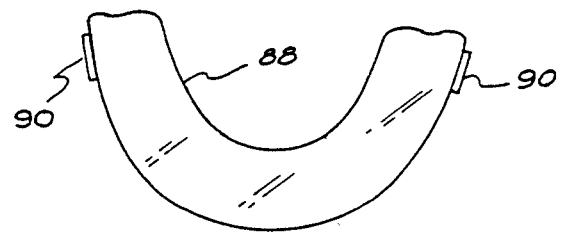
FIG. 29 is a view of an optional feature incorporated in the appliance.

As an aid to the removal of an appliance 88, FIG. 29 shows an option in which thumb or finger grip regions 90 are provided. These regions can have a characteristic which enables the appliance to be better grasped when it is to be removed. These can be integrally incorporated into the appliance or they could be separate pieces attached to the appliance in any suitable way. The intention is to provide a friction surface against which the person's thumb and/or fingers act when the appliance is being removed. This is desirable because the presence of saliva in the mouth tends to make the appliance slippery.

Figure 30:
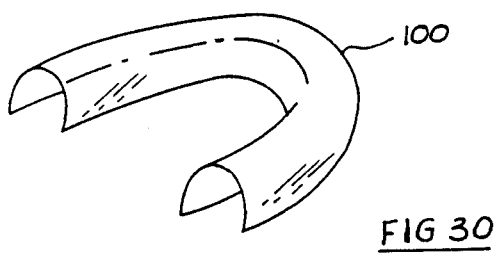
FIG. 30 is a perspective view of an embodiment of the invention as a base plate.

FIG. 30 illustrates the use of the invention as a base plate 100 for a denture. The teeth (not shown) are attached to the base plate material, the teeth being of any conventional synthetic construction known to the art.

The foregoing description of representative embodiments of the invention has been for the purpose of disclosing general principles. A number of specific examples have been shown. Obviously certain modifications, variations and improvements may be indulged in within the scope of the invention. For example, the individual fibers may have different cross sectional shapes. Circular, elliptical, and polygonal are examples of such shapes. Likewise the particular material characteristics can have an influence on the characteristics of any individual appliance, in addition to the particular size and shape of the appliance. Treatment procedures for any given patient will be at the prescription of the attending dentist or orthodontist. Such prescriptions may in fact be a series of individual prescriptions. These may have involved new appliances for each prescription over a course of treatment procedures. Alternatively it is contemplated that it may sometimes be possible to re-process a previously used appliance for an individual so that a subsequent stage of the treatment procedure can be performed without fabricating a completely new appliance. For example, it is contemplated that this can be done by placing an appliance back into a machine and perhaps retreating it, such as by heating, so that it has a slightly different shape suitable for the further stage of the procedure.

The machine for forming the material to the cast may comprise a ram as the force applying means. Another embodiment of machine may comprise a bladder which is pressurized against the sheet to force the sheet into closer conformity with the cast. Heating of the material may be performed from conventional heat sources, but a preferred heating source is by infrared heating.

While a preferred embodiment of the invention has been disclosed, it will be appreciated that principles are applicable to other embodiments.

I claim:

1. The method of making an orthodontic appliance for repositioning teeth of an arch which comprises:
   taking an impression of the arch including the teeth that are to be repositioned and creating from said impression a dental cast in which the teeth to be repositioned are reset to a placement that is desired to be obtained by use of the orthodontic appliance;
   providing a sheet of an elasticized thermoplastic material containing an integral pattern of fibers which are capable of exerting tension forces;
   heating the thermoplastic material to plastic or semi-plastic state, and;
   forming the plastic or semi-plastic material onto said dental cast and allowing the material to cool and assume its relatively more rigid condition.

2. The method set forth in claim 1 including the further step of putting the appliance to use in repositioning those teeth of the arch that are to be repositioned.

3. The method set forth in claim 1 wherein the step of forming the plastic or semi-plastic material onto said dental cast is conducted by forcefully urging the plastic or semi-plastic material onto the dental cast by a force applying means.

4. The method set forth in claim 1 wherein the sheet of thermoplastic material has serrated edge portions which are used for holding the material during heating, and including the further step of trimming the serrated edge portions from the material after the step of forming the material onto the dental cast.

* * * * *